United States Patent [19]

Culbert

[11] Patent Number: Plant 5,366

[45] Date of Patent: Dec. 11, 1984

[54] CHRYSANTHEMUM PLANT NAMED ILLINI SUNSET

[75] Inventor: John R. Culbert, Clinton, Ill.

[73] Assignee: University of Illinois, Chicago, Ill.

[21] Appl. No.: 488,013

[22] Filed: Apr. 25, 1983

[51] Int. Cl.[3] ..... A01H 5/00
[52] U.S. Cl. ..... Plt./74
[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum named Illini Sunset characterized by its flat capitulum form and single capitulum type which is semi-anemone under cool conditions, maroon-pink ray floret color, yellow green to yellow disc florets, 50–65 mm. diameter across face of capitulum, 8–9 week response, short to medium plant height and semi-upright branching pattern, and by its excellent flower production.

1 Drawing Figure

The present invention comprises a new and distinct cultivar of *Chrysanthemum morifolium,* Ramat., named Illini Sunset.

Illini Sunset is a product of a planned breeding program which had the general objectives of creating new chrysanthemum cultivars with single anemone capitulum type, flat form, maroon-pink ray floret color, 8 to 9 week flowering response, and with the ability to produce commercially acceptable quality in a year round pot mum program. Such traits in combination were not present in previously available commercial cultivars.

Illini Sunset was originated from a hybridization made in a controlled breeding program in Urbana, Ill. in 1976. The female parent was identified as 24-01-74 and the male parent as 18-01-74. Illini Sunset was discovered and selected as one flowering plant within the progeny of the selected parentage by John R. Culbert in June, 1977 in a controlled environment in Urbana, Ill., and subsequently, given the code name FP-Ill-76-107-BS.

The first act of asexual reproduction of Illini Sunset was accomplished when vegetative cuttings were taken from the initial selection in September, 1977 in a controlled environment in Urbana, Ill. by a technician working under formulations established and supervised by John R. Culbert. Horticultural examination of selected units initiated Dec. 28, 1977 has demonstrated that the combination of characteristics as herein disclosed for Illini Sunset are firmly fixed and are retained through successive generations of asexual reproduction.

Illini Sunset has not been observed under all possible environmental conditions. The phenotype may vary significantly with variations in environment such as temperature, light intensity, and day length. The following observations, measurements and comparisons describe plants grown in Urbana and West Chicago, Ill. and Parrish, Fla. under greenhouse conditions which approximate those generally used in commercial practice.

The following traits have been repeatedly observed and are determined to be basic characteristics of Illini Sunset, which in combination distinguish this chrysanthemum as a new and distinct cultivar:

1. Flat capitulum form.
2. Single capitulum type, semi-anemone when grown under cool conditions.
3. Maroon-pink ray floret color.

4. Yellow green (immature) to yellow (mature) disc floret color. When exhibiting anemone form, mature disc florets are yellow with maroon streaks.
5. Diameter across face of capitulum 50–65 mm.
6. 8 week winter and 9 week summer flowering response.
7. Short to medium pot plant height of about 250 mm.
8. Semi-upright branching pattern.
9. Excellent flower production.

Of the many commercial cultivars known to the present inventor, the most similar in comparison to Illini Summer is Illini Harvest, the characteristics of which are disclosed in my pending application. Reference is made to attached Chart A which compares certain characteristics of Illini Summer to those same characteristics of Illini Harvest. In general comparison to Illini Harvest, Illini Sunset has maroon-pink flower color, an earlier response, and the disc florets are smaller in diameter when in anemone form.

The accompanying photographic drawings show typical inflorescence and foliage characteristics of Illini Sunset, with colors being as nearly true as possible with illustrations of this type.

In the following description color references are made to The Royal Horticultural Society Colour Chart. The color values were determined between 10:00–10:30 A.M. on Feb. 18, 1983 under 800–1000 ft. candles natural light at Parrish, Fla.

CLASSIFICATION

Botanical: *Chrysanthemum morifolium,* Ramat., cv Illini Sunset.

Commercial: Daisy pot mum.

INFLORESCENCE

Capitulum

*Form.*—Flat, rather narrow, non-spooned ray florets, 25–30 in numbers depending on season and culture.

*Type.*—Single, anemone.

*Diameter across face.*—50–65 mm. When grown as spray on pinched plant.

*Number.*—Normally 25–30 flowers per plant as sprays on pinched plant, although range can be 22–40 depending on growing conditions.

Corolla of ray florets:

*Color (general tonality from a distance of three meters).*—Maroon-pink.

*Color (abaxial).*—65C; Color retention only fair.

*Color (adaxial).*—59C, Fading to 64C.

Corolla of disc florets:

*Color (mature).*—Yellow; when in anemone form yellow with maroon streaks.

*Color (immature).*—Yellow green.

Reproductive organs:

*Androecium.*—Present in disc florets only.

*Gynoecium.*—Present in both ray and disc florets.

PLANT

General appearance: Short to medium, and upright; slightly spreading, height 250 mm. from edge of pot.

Foliage:

*Color (abaxial).*—147B.

*Color (adaxial).*—147A.

*Shape.*—Deeply lobed and slightly serrated; quantity plentiful.

CHART A

COMPARISON OF ILLINI HARVEST AND ILLINI SUNSET

| | | | DIAMETER ACROSS |
|---|---|---|---|

CHART A-continued

COMPARISON OF ILLINI HARVEST AND ILLINI SUNSET

| CULTIVAR | RAY FLORET COLOR | CAPITULUM TYPE & FORM | FACE OF CAPITULUM |
|---|---|---|---|
| ILLINI HARVEST | Dark Bronze | Flat daisy or semi-anemone type when grown cool | 50–65 mm. |
| ILLINI SUNSET | Maroon-Pink | Flat daisy anemone type when grown cool | 55–65 mm. |

| CULTIVAR | PLANT HEIGHT | FLOWERING RESPONSE PERIOD | DIAMETER ACROSS DISC, ANEMONE FORM |
|---|---|---|---|
| ILLINI HARVEST | 280 mm. | 9 weeks | 22–26 mm. |
| ILLINI SUNSET | 250 mm. | 8 weeks | 15–18 mm. |

Comparison made of plants grown as 6" pot plants in Parrish, Florida

I claim:

1. A new and distinct cultivar of chrysanthemum named Illini Sunset, as described and illustrated, and particularly characterized by its flat capitulum form and single capitulum type which is semi-anemone under cool conditions; maroon-pink ray florets; 50–65 mm. diameter across face of capitulum; 8–9 week response; short to medium plant height and semi-upright branching pattern, and by its excellent flower production.

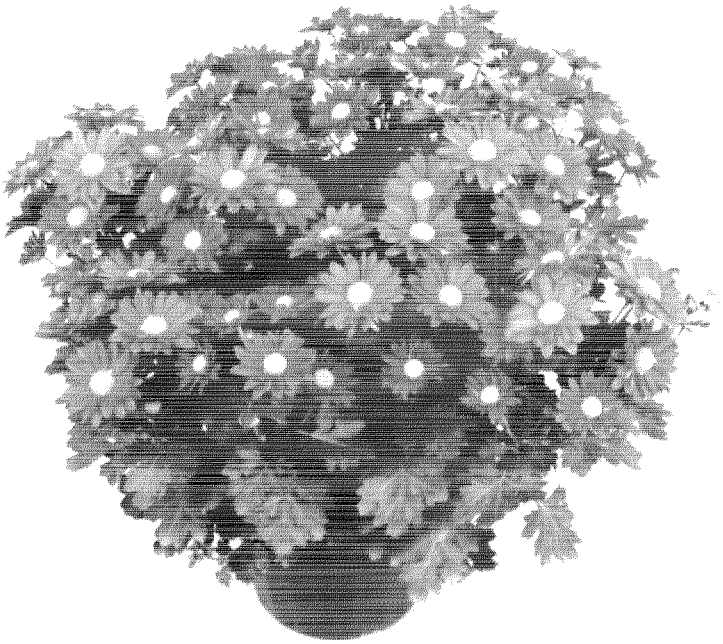

* * * * *